United States Patent
Staffel et al.

(10) Patent No.: US 12,214,103 B2
(45) Date of Patent: Feb. 4, 2025

(54) PRODUCTS FOR TREATING BLEEDING WOUNDS

(71) Applicants: BK GIULINI GMBH, Ladenburg (DE); FKuR PROPERTY GMBH, Willich (DE)

(72) Inventors: Thomas Staffel, Grünstadt (DE); Henrike Thauern, Weinheim (DE); Juergen Straub, Mannheim (DE); Edmund Dolfen, Willich (DE); Carmen Michels, Willich (DE); Karel Krpan, Willich (DE); Frank-Martin Neumann, Willich (DE)

(73) Assignees: BK GIULINI GMBH, Ladenburg (DE); FKuR PROPERTY GMBH, Willich (DE)

(*) Notice: Subject to any disclaimer, the term of this patent is extended or adjusted under 35 U.S.C. 154(b) by 785 days.

(21) Appl. No.: 17/416,263

(22) PCT Filed: Dec. 19, 2019

(86) PCT No.: PCT/EP2019/086325
§ 371 (c)(1),
(2) Date: Jun. 18, 2021

(87) PCT Pub. No.: WO2020/127745
PCT Pub. Date: Jun. 25, 2020

(65) Prior Publication Data
US 2022/0105233 A1   Apr. 7, 2022

(30) Foreign Application Priority Data

Dec. 20, 2018 (EP) .................................... 18214785
Aug. 23, 2019 (EP) .................................... 19193416

(51) Int. Cl.
*A61L 24/00* (2006.01)

(52) U.S. Cl.
CPC ....... *A61L 24/0084* (2013.01); *A61L 24/0031* (2013.01); *A61L 2400/04* (2013.01)

(58) Field of Classification Search
CPC .............. A61L 24/0084; A61L 24/0031; A61L 2400/04; A61L 24/001; C08L 67/02; C08L 67/04
See application file for complete search history.

(56) References Cited

U.S. PATENT DOCUMENTS

| | | |
|---|---|---|
| 4,822,349 A | 4/1989 | Hursey et al. |
| 9,907,879 B2 | 3/2018 | Thauern et al. |
| 2003/0133990 A1 | 7/2003 | Hursey et al. |
| 2006/0039994 A1 | 2/2006 | Davis |
| 2006/0198837 A1 | 9/2006 | Morrissey et al. |
| 2016/0053112 A1 | 2/2016 | Liu et al. |
| 2016/0263275 A1 | 9/2016 | Thauern et al. |

FOREIGN PATENT DOCUMENTS

| | | |
|---|---|---|
| JP | 2007169171 A | 7/2007 |
| JP | 2008531692 A | 8/2008 |
| JP | 2010081979 A | 4/2010 |
| JP | 2011512394 A | 4/2011 |
| JP | 2016535041 A | 11/2016 |
| WO | 2006088912 A2 | 8/2006 |
| WO | 2006096345 A2 | 9/2006 |
| WO | 2009104005 A1 | 8/2009 |
| WO | 2015063190 A1 | 5/2015 |

OTHER PUBLICATIONS

Lawton, G., et al., "Novel Haemostatic Dressings", JR Army Med Corps 155(4), 309-314 (2009).
Patent Cooperation Treaty, International Searching Authority, Search Report and Written Opinion for PCT/EP2019/086325, 2 pages, English Translation, dated Mar. 17, 2020.
Wright, J., et al., "Thermal injury resulting from application of a granular mineral hemostatic agent", J Trauma 57(2), 224-230, Abstract, 1 page (2004).
Khatsee, S., et al., "Electrospinning polymer bled of PLA and PBAT: Electrospinnability-solubility map and effect of polymer solution parameters toward application as antibiotic-carrier mats", J Appl Polym Sci 135 (46486), 19 pages (2018).

*Primary Examiner* — Robert A Wax
*Assistant Examiner* — Quanglong N Truong
(74) *Attorney, Agent, or Firm* — Viksnins Harris Padys Malen LLP

(57) ABSTRACT

The invention relates to products in the form of pads or films for treating bleeding wounds, said products being formed from an organic polymer material that contains at least one particulate, crystalline inorganic polyphosphate finely divided in the organic polymer material, and the polyphosphate having a solubility in deionized water at 20° C. of less than 5 g/L, particularly less than 1 g/L, and the anion of the polyphosphate on average (number average) having at least four phosphorus atoms per polyphosphate anion.

20 Claims, No Drawings

PRODUCTS FOR TREATING BLEEDING WOUNDS

The present invention relates to agents for treating bleeding wounds in mammals, in particular for treating bleeding wounds in humans and especially in patients whose blood clotting has been affected by the administration of anticoagulants.

Injuries to human and animal tissue layers can damage the blood vessels within them, which can result in an escape of blood at the affected site on the skin or inside the body. After a phase of blood escape, natural blood clotting commences. Blood clotting refers to the solidification of liquid blood as a physiological protective mechanism. Blood clotting is based on two complex, cascading enzymatic reaction pathways in which a number of coagulation factors are involved. Both pathways, which are generally known as the intrinsic pathway and the extrinsic pathway, lead to the formation of insoluble fibrin strands, which play a major role in the formation of the blood clots responsible for wound closure. Thrombin, also known as coagulation factor IIa, plays a key role here, since it not only causes the formation of fibrin, but also has an activating effect at several points in the coagulation cascade through positive feedback. Factor XII, also known as Hageman factor, acts on the other hand at the start of the intrinsic pathway of the coagulation cascade and ultimately triggers the formation of thrombin from prothrombin.

Natural blood clotting commences almost immediately after the trauma has occurred, but is a relatively slow process that takes some time to bring about wound closure and the accompanying hemostasis. In many cases, accelerated hemostasis is therefore desirable, for example for hygiene reasons or when excessive blood loss is feared on account of the size of the wound or the strength of the blood flow. Well-known methods of hemostasis, such as covering the wound, applying pressure bandages and staples, or suturing the wound, are often inadequate and—particularly in the case of injury to vessels in internal organs—possible only with difficulty or not at all. Methods intended to help improve hemostasis are accordingly known from the prior art, for example the introduction of substances that promote blood clotting, such as fibrin glue, into the wound area.

The use of inorganic substances as hemostatic agents has been repeatedly described. For example, U.S. Pat. No. 4,822,349 and US 2003/0133990 describe the use of agents based on dehydrated zeolites for treating bleeding wounds. It is postulated that the dehydrated zeolite triggers blood clotting by absorbing water from the escaping blood, with the heat released in this process promoting wound closure. Such agents were for a period marketed under the trade name QuickClot®. Use was however accompanied on a number of occasions by severe tissue damage (see J. K. Wright et al., J. Trauma 57 (2004), 224-230). A reduction in the drawbacks of agents based on dehydrated zeolites is achieved by the molecular sieves based on aluminum phosphate described in US 2006/0039994.

WO 2006/088912 describes the hemostatic effect of clay minerals such as bentonite or kaolin. Corresponding hemostatic agents based on kaolin have been marketed under the trade name Woundstat®. Here, too, it is thought that blood clotting is triggered by the absorption of water from the escaping blood, with mechanical wound closure brought about by the polyacrylic acid also present in these agents. These agents are however no longer in use, on account of the occurrence of tissue damage and the development of embolisms (see G. Lawton et al., JR. Army Med. Corps 155 (4) (2009) 309-314 with further evidence).

WO 2015/063190 describes the hemostatic effect of crystalline, water-insoluble inorganic polyphosphates. The hemostatic effect of these polyphosphates is thought to be based on contact activation of the coagulation cascade, this being presumably mediated by factor XII, which in turn triggers thrombin formation and thus the formation of fibrin from fibrinogen via the intrinsic pathway. These polyphosphates are typically applied in the form of a powder.

In the case of bleeding wounds, the handling of particulate substances such as powders is however problematic. For example, if bleeding is profuse there is a risk that the substance will be quickly washed away from the wound area and thus lose its effectiveness, whereas if bleeding is lighter it may penetrate the bloodstream and cause undesirable effects in parts of the body well away from the wound, such as the formation of thrombotic blood clots.

The object of the invention is therefore to provide an agent that is easy to handle and has a hemostatic effect, but without the disadvantages of the prior art. It should be possible to use the agent in both lightly and heavily bleeding wounds in humans, in particular in surgical wounds and/or in patients in whom blood clotting has been lowered by the administration of anticoagulants. The agent should efficiently still the bleeding that occurs. In addition, it should be easy and inexpensive to manufacture and be easy and reliable to use in medical practice using conventional methods.

Surprisingly, the hemostatic effect of crystalline, water-insoluble inorganic polyphosphates, such as those described in WO 2015/063190, is not lost when they are embedded in finely divided form in a polymer matrix. This allows, for example, the production of pads or films having a hemostatic effect, which can be applied more easily than corresponding powders to bleeding wounds in mammals, in particular humans.

This is surprising because, as already mentioned, it must be assumed that the hemostatic effect of water-insoluble inorganic polyphosphates is based on contact activation of factor XII.

The present invention accordingly relates to agents in the form of flexible sheet materials, in particular in the form of pads or films, that are formed from an organic polymer material comprising at least one particulate crystalline inorganic polyphosphate present in the organic polymer material in finely divided form, the polyphosphate at 20° C. having a solubility in deionized water of less than 5 g/L, in particular less than 1 g/L and the anion of the polyphosphate having an average (number average) of at least four phosphorus atoms per polyphosphate anion.

The invention relates in particular to the use of such agents for treating bleeding wounds in mammals, in particular for treating bleeding wounds in humans and especially in patients whose blood clotting has been affected by the administration of anticoagulants.

Sheet materials are generally understood as meaning macroscopic sheet-like structures having areas of usually at least 1 cm², in particular at least 2 cm² or at least 3 cm². The area upper limit is of altogether lesser importance. For use according to the invention, the area of the structure usually does not exceed a value of 2000 cm², and especially 1000 cm². In particular, it is within a range from 1 to 2000 cm² or within a range from 2 to 1500 cm² or within a range from 3 to 1000 cm². The thickness can be varied over wide ranges and, depending on the type of sheet material, is within a range from 1 μm to 20 mm, in particular within a range from 10 µm to 10 mm. The determination of the thickness can be determined in a manner known per se. The values stated here are average thickness values determined at a minimum of five different test points on the sheet material.

The sheet materials of the invention are flexible, i.e. they can undergo elastic deformation under the action of mechanical forces, at least with respect to their surface normal. This deformability is ensured by the sheet material being formed from a polymer material that has suitable elasticity in respect of its dimensions, in particular its thickness. The modulus of elasticity of typical polymer materials is typically within a range from 0.001 to 3.0 GPa at 20° C., in particular within a range from 0.1 to 1.2 GPa.

According to the invention, the sheet materials are formed from an organic polymer material in which the particulate crystalline inorganic polyphosphate is present in finely divided form. In contrast to textile sheet materials that are made up of fibers, in the sheet materials of the invention the organic polymer material forms a sheet-like matrix in which the particles of the particulate crystalline inorganic polyphosphate, hereinafter referred to as polyphosphate particles, are present in finely divided form or in which the polyphosphate particles are embedded in finely divided form. In other words, the organic polymer material forms a coherent layer in which the polyphosphate particles are embedded. The polyphosphate particles can here be completely or partially surrounded by the organic polymer material.

Typical flexible sheet materials are films and pads. Films are understood as meaning sheet materials having a thickness of usually not more than 1 mm, frequently not more than 500 µm, in particular not more than 250 µm or 200 µm, e.g. thicknesses within a range from 1 to 1000 µm, frequently 5 to 500 µm, in particular within a range from 10 to 250 µm or within a range from 20 to 200 µm. Pads are cushion-shaped sheet materials having thicknesses above 1 mm, e.g. thicknesses within a range from 1 to 20 mm, in particular within a range from 2 to 10 mm.

All of the crystalline inorganic polyphosphates described in WO 2015/063190 that are crystalline and essentially insoluble in water, i.e. at 20° C. having a solubility in deionized water of less than 5 g/L, in particular less than 1 g/L, are in principle suitable as polyphosphates.

The inorganic polyphosphates present in the sheet materials of the invention are crystalline and usually have a degree of crystallinity of at least 90%, preferably at least 95%, and in particular at least 98%. The degree of crystallinity of the polyphosphate can be determined by X-ray powder diffractometry in a manner known per se, for example according to the method described in WO 2015/063190. In this method, the half-widths of the detected reflections in the diffractograms are used to quantify the crystallinity in a manner known per se.

The polyphosphate anions of the crystalline inorganic polyphosphates present in the sheet materials of the invention typically have an average (number average) of at least 6, in particular at least 8 or at least 10, and especially at least 12 or at least 15, phosphorus atoms per polyphosphate anion. Those skilled in the art know that the polyphosphate anions in polyphosphates of this kind typically do not all have the same number of phosphorus atoms per anion, but instead differ in the number of phosphorus atoms per polyphosphate anion. In particular, the polyphosphate anions of the polyphosphates of the invention have an average (number average) of 4 to 2000, frequently 6 to 1000 or 8 to 500, preferably 10 to 400 or 12 to 300, and in particular 15 to 200, phosphorus atoms per polyphosphate anion. The number-average number of phosphorus atoms in the polyphosphate anion can be determined in a manner known per se, e.g. by $^{31}P$ solid-state NMR, for example using the method described in WO 2015/063190.

The crystalline inorganic polyphosphates are preferably selected from crystalline alkali metal polyphosphates, alkaline earth metal polyphosphates, and ammonium polyphosphates that are essentially insoluble in water. The cations of the crystalline polyphosphates are accordingly preferably alkali metal, alkaline earth metal or ammonium ions, selected in particular from $Na^+$, $K^+$, $NH_4^+$, $Ca^{2+}$, and $Mg^{2+}$, and preferably from $Na^+$, $K^+$, $NH_4^+$, and $Ca^{2+}$.

The anions of the water-insoluble crystalline inorganic polyphosphates are usually essentially linear or cyclic, i.e. to an extent of at least 80 mol %, preferably at least 90 mol %, and in particular at least 95 mol %, based on the total amount of polyphosphate anions in the crystalline polyphosphate. The anions of such polyphosphates are accordingly chains of metaphosphate units $PO_3^-$ in which any two phosphorus atoms are connected to one another via an oxygen atom. The "chain length" is accordingly understood as meaning the number of metaphosphate units $PO_3^-$ present in the polyphosphate anion. The linear crystalline polyphosphates of the invention can be described by formula A:

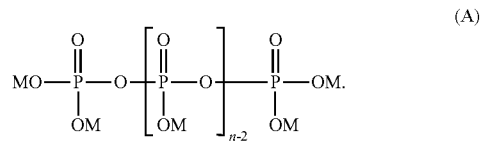

(A)

In formula A, n represents a number averaging (number average) 4 to 2000, frequently 6 to 1000 or 8 to 500, preferably 10 to 400 or 12 to 300, and in particular 15 to 200. M represents a cation or cation equivalent preferably selected from alkali metal, alkaline earth metal and ammonium ions, from $Na^+$, $K^+$, $NH_4^+$, $½Ca^{2+}$ and $½Mg^{2+}$, and preferably from $Na^+$, $K^+$, $NH_4^+$ and $½Ca^{2+}$. The expressions "$½Ca^{2+}$" and "$½Mg^{2+}$" here mean that each $Ca^{2+}$ or $Mg^{2+}$ present in the polyphosphate of the formula A represents two cations M in formula A on account of its doubly positive charge.

The crystalline inorganic polyphosphate is preferably selected from crystalline, inorganic sodium polyphosphates, in particular linear sodium polyphosphates of the formula A. In particular, the crystalline inorganic polyphosphate is a so-called Maddrell salt, also known as Maddrell's salt. Maddrell salt, also known as Maddrell's salt, is understood by those skilled in the art as meaning a highly condensed linear sodium polyphosphate typically having an average of at least 20 phosphorus atoms per polyphosphate anion.

The crystalline polyphosphates present in the pads and films of the invention are characterized by their high purity. They accordingly comprise only small amounts of water-soluble constituents. Constituents referred to here as water soluble are ones that, in powder form, dissolve in water at 25° C. at a rate of at least 50% by weight per hour. Such water-soluble constituents are typically mono-, pyro- and triphosphates and also cyclic metaphosphates, such as tri-, tetra- or hexametaphosphates, that have high solubility in water. The proportion of water-soluble constituents is usually less than 8% by weight, preferably less than 5% by weight, and in particular less than 3% by weight, based on the total weight of polyphosphate. The proportion of water that may still be present in the crystalline polyphosphate in the form of residual moisture is normally less than 1% by weight, preferably less than 0.5% by weight, and in particular less than 0.3% by weight, based on the total weight of polyphosphate. The proportion of ingredients that are not (poly)phosphates or water is usually less than 0.1% by weight, preferably less than 0.05% by weight, and in particular less than 0.01% by weight, based on the total weight of polyphosphate.

The crystalline inorganic polyphosphates present in the agents of the invention are present in the polymer material that forms the sheet material in finely divided form, i.e. in the form of crystalline polyphosphate particles. The polymer material accordingly typically forms a continuous matrix that surrounds or at least partially surrounds the polyphosphate particles distributed therein.

The particle size of the crystalline inorganic polyphosphate particles usually corresponds to the crystalline inorganic polyphosphate used for its production. The crystalline polyphosphate particles typically have particle sizes within a range from 0.1 to 80 µm, in particular within a range from 0.3 to 50 µm. The crystalline polyphosphate particles normally have a mass-median particle diameter within a range from 3 to 50 µm, in particular within a range from 5 to 40 µm, and especially 10 to 30 µm. The values stated here are the so-called $d_{50}$ values of the integral mass distribution of the particle sizes/grain sizes of the crystalline inorganic polyphosphate used for production.

The particle size distribution of the crystalline inorganic polyphosphate particles is typically determined by static laser-light scattering in accordance with the method described in ISO 13320:2009. The mass fractions of the respective grain sizes can be determined therefrom. Alternatively, the mass fractions of the respective grain sizes or grain size ranges can be determined in accordance with DIN 66165:2016-08 by fractionation of the polyphosphate using a plurality of sieves by means of machine sieving in pre-calibrated systems. Unless otherwise specified here and hereinbelow, the particle size distribution of particulate substances is determined by static laser-light scattering in accordance with the method described in ISO 13320:2009.

Unless otherwise specified, percentages relating to particle sizes/grain sizes are to be understood as meaning percentages by weight. In this context, the $d_{90}$ value refers to the grain size/particle size below which 90% by weight of the polyphosphate particles fall. The $d_{10}$ value refers to the grain size/particle size below which 10% by weight of the polyphosphate particles fall. The $d_{50}$ value refers to the mass-median grain size/particle size of the granulate. The particle size distribution of the crystalline polyphosphate used for production preferably has a $d_{90}$ value of max. 70 µm, in particular max. 50 µm, and especially max. 40 µm. The particle size distribution of the crystalline polyphosphate used for production preferably has a $d_{10}$ value of at least 0.5 µm, in particular at least 1 µm, and especially at least 2 µm.

The agents of the invention typically comprise the crystalline inorganic polyphosphate in an amount within a range from 1% to 30% by weight, in particular in an amount within a range from 2% to 20% by weight and especially in an amount within a range from 3% to 15% by weight, based on the total weight of the agent.

The organic polymer materials that make up the sheet material are usually thermoplastic polymer materials or hydrogels based on organic polymers.

In a first group of embodiments of the invention, the polymer materials are thermoplastic polymer materials. These normally consist of at least 50% by weight, based on the total mass of polymer material+polyphosphate, of one or more organic thermoplastic polymers. In particular, the proportion of organic thermoplastic polymers in thermoplastic polymer materials of this kind is at least 60% by weight and especially at least 65% by weight, based on the total mass of polymer material+polyphosphate. The proportion of organic thermoplastic polymers in thermoplastic polymer materials of this kind is frequently 50% to 99% by weight, in particular at least 60% to 97% by weight, and especially 65% to 95% by weight, based on the total mass of polymer material+polyphosphate. In this group of embodiments, the polyphosphate content in the agents of the invention is typically within a range from 1% to 30% by weight, in particular within a range from 2% to 20% by weight, and especially within a range from 3% to 15% by weight, based on the total mass of polymer material+polyphosphate.

Examples of suitable organic thermoplastic polymers in thermoplastic polymer materials are primarily condensation polymers such as polyesters, including aliphatic polyesters, partially aromatic polyesters and also aromatic polyesters, additionally polyamides, including aliphatic polyamides and partially aromatic polyamides, polyesteramides, including aliphatic polyesteramides and partially aromatic polyesteramides, polycarbonates, polyester carbonates, but also addition polymers such as polystyrenes, polyacrylates, polyolefins, including polyethylene such as HDPE, LDPE, LLDPE, HMW, and UHMW, polypropylenes, such as atactic, syndiotactic or isotactic polypropylene, and polyisoprenes, e.g. atactic, syndiotactic or isotactic polyisoprene, polyureas, and polyurethanes, including polyester urethanes and polyether urethanes, also polysiloxanes and blends of the abovementioned polymers. Preferred thermoplastic polymers are selected from polyhydroxyalkanoates, polylactides, aliphatic-aromatic polyesters, aliphatic-aromatic polyamides, polyolefins, and/or mixtures thereof. In particular, the polymer material comprises at least one condensation polymer selected in particular from polyesters and polyester carbonates and mixtures thereof.

The thermoplastically processable polymer material preferably comprises at least one organic polymer having a glass transition temperature or melting point within a range from 75 to 250° C. If the polymer has a melting point, i.e. is partially crystalline or crystalline, it preferably has a melting point within a range from 75 to 250° C. If the polymer is amorphous, it preferably has a glass transition temperature within a range from 75 to 250° C. The melting point or the glass transition temperature is normally determined by dynamic differential calorimetry (DSC) in accordance with DIN EN ISO 11357:2017.

In a preferred embodiment of the invention, the thermoplastically processable polymer material comprises as the principal constituent, i.e. to an extent of at least 50% by weight, in particular to an extent of at least 60% by weight, especially to an extent of at least 80% by weight or to an extent of at least 90% by weight, based on the organic polymers contained therein, at least one polymer selected from polyhydroxyalkanoates, polylactides, aliphatic-aromatic polyesters, aliphatic-aromatic polyamides, polyolefins, and/or mixtures thereof.

In this preferred embodiment of the invention, the thermoplastically processable polymer material comprises as the principal constituent in particular:

i. a mixture of at least one polylactide and at least one aliphatic-aromatic polyester;

or
ii. at least one copolyester of a hydroxybutyric acid with a hydroxyalkanoic acid having 6 to 12 carbon atoms, or a mixture of such a copolyester with polylactide;
or
iii. at least one polyolefin, preferably polyethylene or polypropylene;
Or
iv. syndiotactic, isotactic, or atactic polyisoprene;
or
v. polysiloxane.

In a preferred embodiment of the invention, the thermoplastically processable polymer material comprises as the principal constituent, i.e. to an extent of at least 50% by weight, in particular to an extent of at least 60% by weight, especially to an extent of at least 80% by weight or to an extent of at least 90% by weight, based on the organic polymers contained therein, at least one biodegradable polymer.

The term "biodegradable" is understood as meaning that the substance concerned, in this case the polymer, in the test of OECD Guideline 301B from 1992 (measurement of $CO_2$ evolution during composting in a mineral sludge and comparison with the theoretically maximum possible $CO_2$ evolution), is at least 5% degraded after seven days at 25° C.

Examples of preferred biodegradable polymers are polyhydroxyalkanoates, polylactides, aliphatic-aromatic polyesters, aliphatic-aromatic polyamides, aliphatic-aromatic polyesteramides, and mixtures thereof. In particular, the biodegradable polymer is selected from aliphatic-aromatic polyesters and mixtures thereof with polyhydroxyalkanoates and/or polylactides.

Partially aromatic polyesters are also referred to as aliphatic-aromatic polyesters, i.e. polyesters based on aromatic dicarboxylic acids and aliphatic dihydroxy compounds and also polyesters based on mixtures of aromatic dicarboxylic acids with aliphatic dicarboxylic acids and aliphatic dihydroxy compounds. Aliphatic-aromatic polyesters are in particular polyesters based on mixtures of aliphatic dicarboxylic acids with aromatic dicarboxylic acids and aliphatic dihydroxy compounds.

Aliphatic dicarboxylic acids are for example oxalic acid, malonic acid, succinic acid, 2-methylsuccinic acid, glutaric acid, 2-methylglutaric acid, 3-methylglutaric acid, α-ketoglutaric acid, adipic acid, pimelic acid, azelaic acid, sebacic acid, brassylic acid, fumaric acid, 2,2-dimethylglutaric acid, suberic acid, diglycolic acid, oxaloacetic acid, glutamic acid, aspartic acid, itaconic acid, maleic acid, and mixtures thereof. Preferred aliphatic dicarboxylic acids are selected from succinic acid, adipic acid, azelaic acid, sebacic acid, brassylic acid, and mixtures thereof.

The aromatic dicarboxylic acid is in particular terephthalic acid.

Aliphatic diols are in particular branched or linear alkanediols having 2 to 12 carbon atoms, in particular 4 to 6 carbon atoms. Examples of suitable alkanediols are ethylene glycol, propane-1,2-diol, propane-1,3-diol, butane-1,2-diol, butane-1,4-diol, pentane-1,5-diol, 2,4-dimethyl-2-ethylhexane-1,3-diol, 2,2-dimethylpropane-1,3-diol, 2-ethyl-2-butylpropane-1,3-diol, 2-ethyl-2-isobutylpropane-1,3-diol, 2,2,4-trimethylhexane-1,6-diol, especially ethylene glycol, propane-1,3-diol, butane-1,4-diol and 2,2-dimethylpropane-1,3-diol (neopentyl glycol).

The aliphatic-aromatic polyester is particularly preferably selected from polybutylene azelate-co-butylene terephthalate (PBAzeT), polybutylene brassylate-co-butylene terephthalate (PBBrasT), polybutylene adipate terephthalate (PBAT), polybutylene sebacate terephthalate (PBSeT), and polybutylene sebacate terephthalate (PBSeT) and mixtures thereof.

Polylactides include polylactic acid and polylactic acid copolymers such as polylactide-co-polyglycolic acid (PLGA). Polyhydroxyalkanoates include in particular homo- and copolyesters of 3- or 4-hydroxyalkanoic acids having 4 to 12 carbon atoms, for example polyhydroxybutyrates such as poly-4-hydroxybutyrates and poly-3-hydroxybutyrates, polyhydroxyvalerates such as homo- and copolyesters of 3-hydroxyvaleric acid, polyhydroxyhexanoates such as homo- and copolymers of 3-hydroxyhexanoic acid. Particularly preference among these is given in particular to copolyesters of the abovementioned hydroxybutyric acids with longer-chain hydroxyalkanoic acids having preferably 6 to 12 carbon atoms, for example copolyesters of a hydroxybutyric acid with a hydroxyvaleric acid, e.g. (P(3HB)-co-P(3HV)), and also copolyesters of a hydroxybutyric acid with a hydroxyhexanoic acid.

Partially aromatic polyamides are also referred to as aliphatic-aromatic polyamides, i.e. polyamides based on aromatic dicarboxylic acids and aliphatic diamino compounds and also polyamides based on combinations of aromatic dicarboxylic acids with aliphatic dicarboxylic acids and aliphatic diamino compounds.

Partially aromatic polyesteramides are also referred to as aliphatic-aromatic polyesteramides, i.e. polyesteramides based on aromatic dicarboxylic acids and combinations of aliphatic dihydroxy compounds and aliphatic diamino compounds and also polyesteramides based on combinations of aromatic dicarboxylic acids with aliphatic dicarboxylic acids and combinations of aliphatic dihydroxy compounds and aliphatic diamino compounds.

Aliphatic-aromatic polyesters are in particular polyesters based on mixtures of aliphatic dicarboxylic acids with aromatic dicarboxylic acids and aliphatic dihydroxy compounds.

The thermoplastically processable organic polymer materials preferably comprise, based on the organic polymers contained therein, at least one aliphatic-aromatic polyester, in particular at least one of the aliphatic-aromatic polyesters mentioned as being particularly preferred. In particular, the at least one aliphatic-aromatic polyester is the principal constituent and makes up at least 50% by weight, in particular at least 60% by weight, based on the organic polymers present in the polymer material.

In particular, the thermoplastically processable organic polymer materials comprise as the principal constituent, i.e. to an extent of at least 50% by weight, preferably to an extent of at least 60% by weight, in particular to an extent of at least 80% by weight or to an extent of at least 90% by weight, based on the organic polymers contained therein, a mixture of at least one polylactide and at least one aliphatic-aromatic polyester, in particular at least one of the aliphatic-aromatic polyesters mentioned as being particularly preferred.

In a preferred group of embodiments, the thermoplastically processable organic polymer materials comprise as the principal constituent, i.e. to an extent of at least 50% by weight, preferably to an extent of at least 60% by weight, in particular to an extent of at least 80% by weight or to an extent of at least 90% by weight, based on the organic polymers contained therein, a mixture comprising:
  1% to 40% by weight, in particular 2% to 30% by weight, of at least one polylactide and
  60% to 99% by weight, in particular 70% to 98% by weight, of at least one aliphatic-aromatic polyester, in particular at least one of the aliphatic-aromatic polyesters mentioned as being particularly preferred.

where the values in % by weight are based on the total mass of polylactide and aliphatic-aromatic polyester.

In a further preferred group of embodiments, the thermoplastically processable organic polymer materials comprise as the principal constituent, i.e. to an extent of at least 50% by weight, preferably to an extent of at least 60% by weight, in particular to an extent of at least 80% by weight or to an extent of at least 90% by weight, based on the organic polymers contained therein, at least one copolyester of a hydroxybutyric acid with a hydroxyalkanoic acid having 6 to 12 carbon atoms, for example at least one copolyester of a hydroxybutyric acid with a hydroxyvaleric acid, e.g. (P(3HB)-co-P(3HV)), and/or a copolyester of a hydroxybutyric acid with a hydroxyhexanoic acid, or a mixture of one or more such copolyesters with at least one polylactide.

In addition to the organic polymer, the polymer material may also comprise typical processing aids.

Processing aids include dispersants, lubricants, hydrophobing agents, phase promoters, crosslinkers, mixing improvers, plasticizers, catalysts, and antioxidants and also chain extenders. The processing aids are preferably physiologically compatible and/or have been licensed for use in medical devices.

In addition to the polymer material and the polyphosphate, the agents based on thermoplastic polymer materials may optionally comprise fillers other than inorganic polyphosphate. Further fillers include in particular inorganic fillers such as those normally used in thermoplastic polymer materials. The further fillers are preferably physiologically compatible and/or have been licensed for use in medical devices. Examples of suitable fillers are chalk, silica gel, and clay minerals such as talc, or bentonite and mixtures thereof.

The other fillers normally have a mass-median particle diameter ($d_{50}$ value) within a range from 3 to 50 µm, in particular within a range from 5 to 40 µm and especially 10 to 30 µm, determined by static laser-light scattering in accordance with the method described in ISO 13320:2009 or in accordance with DIN 66165:2016-08 by fractionation of the filler using a plurality of sieves by means of machine sieving in precalibrated systems.

The proportion of processing aids is typically within a range from 0% to 5% by weight. The proportion of further fillers is typically within a range from 0% to 25% by weight or within a range from 1% to 25% by weight, based on the total mass of polymer material+polyphosphate+further filler. The total mass of polyphosphate and fillers different therefrom is typically within a range from 1% to 50% by weight, in particular within a range from 2% to 40% by weight, and especially within a range from 3% to 35% by weight, based on polymer material+polyphosphate+further filler.

In a second group of embodiments of the invention, the polymer material is a hydrogel based on organic polymers. These are water-containing gels based on crosslinked, water-swellable, but at the same time water-insoluble polymers, which are also referred to as hydrogel formers (see Römpp Chemie-Lexikon, 10th edition, Georg Thieme Verlag 1997, p. 1835 and literature cited therein).

Suitable hydrogel formers are crosslinked poly(meth)acrylic acids, crosslinked polyvinyl alcohols, crosslinked polyvinylpyrrolidones, crosslinked polyalkylene ethers, and preferably crosslinked polysaccharides such as carrageenan, gellan-agarose, xanthan, starch, chitosan, carboxymethyl cellulose, pectins, and alginates. Overviews of hydrogels based on cross-linked polysaccharides can be found in J. T. Oliveira et al. in "Natural-Based Polymers for Biomedical Applications", Chapter 18: "Hydrogels from polysaccharide-based materials: Fundamentals and applications in regenerative medicine", Woodhead Publishing in Biomaterials 2008, pp. 485-514, https://doi.org/10.1533/9781845694814.4.485 and in D. Pasqui et al., *Polymers* 2012, 4, 1517-1534; doi:10.3390/polym4031517. The crosslinking of the polysaccharide can be effected by covalent crosslinkers and also by coordinative crosslinkers, e.g. by salts of polyvalent metal ions. These include in particular salts of the alkaline earth metals, in particular calcium salts such as calcium chloride, calcium carbonate or calcium sulfate, and also zinc salts such as zinc chloride or zinc sulfate.

Hydrogels preferred according to the invention comprise as the hydrogel former at least one crosslinked polysaccharide, in particular at least one crosslinked carboxylated polysaccharide, such as carboxymethyl cellulose, pectins and alginates, and especially a cross-linked alginate. The crosslinking of the carboxylated polysaccharide is effected in particular by coordinative crosslinkers. In particular, crosslinking is effected by salts of polyvalent metal ions. These include in particular the abovementioned salts of the alkaline earth metals and also the abovementioned zinc salts.

In this second group of embodiments, the agent of the invention typically comprises the hydrogel former in an amount within a range from 1% to 20% by weight, in particular in an amount within a range from 2% to 15% by weight, based on the total mass of hydrogel+polyphosphate. In addition to the hydrogel former, the hydrogel comprises water and the crystalline inorganic polyphosphate. The water content in the hydrogel is preferably within a range from 20% to 80% by weight based on the total mass of hydrogel former, water, and polyphosphate. In this group of embodiments, the polyphosphate content in the agents of the invention is typically within a range from 1% to 30% by weight, in particular within a range from 2% to 20% by weight, and especially within a range from 3% to 15% by weight, based on the total mass of hydrogel former, water, and polyphosphate.

In addition to the abovementioned constituents, the hydrogel-based agent of the invention may comprise further constituents necessary for its production. These include in particular buffers and retarders, e.g. alkali metal pyrophosphates and reaction products formed during the reaction of the uncrosslinked hydrogel former with the crosslinker used, for example inorganic acids and salts thereof.

The agents of the invention may also comprise one or more further agents other than crystalline inorganic polyphosphates that are known to have a hemostatic effect. An overview can be found, for example in G. Lawton et al., JR. Army Med. Corps 155(4) (2009) 309-314, with further evidence. It is preferably an organic agent, for example chitosan, derivatives thereof, thrombin, fibrin or fibrinogen. The proportion of such other agents having a hemostatic effect is usually not more than 10% by weight based on the weight of the agents of the invention and preferably not more than 5% by weight based on the weight of the agents of the invention. In particular, the agents of the invention do not contain any further inorganic agents having a hemostatic effect other than crystalline inorganic polyphosphate.

In a preferred embodiment of the invention, the agents of the invention are used in sterile form. The invention accordingly also relates to agents of the invention that are sterile and to agents of the invention in sterile form that are enclosed in a packaging so that they do not lose their sterility even over relatively long storage periods.

A particularly preferred group of embodiments of the invention relates to films made from the thermoplastic polymer materials described above that comprise at least one crystalline inorganic polyphosphate.

Preferred films have a thickness within a range from 10 to 250 µm, in particular within a range from 20 to 200 µm. In particular, they comprise as the crystalline inorganic polyphosphate a polyphosphate having a mass-median particle diameter $d_{50}$ within a range from 3 to 50 µm, in particular within a range from 5 to 40 µm, and especially 10 to 30 µm. In particular, the particle diameter is adjusted so that the ratio of film thickness to mass-median particle diameter of the particulate polyphosphate is within a range from 0.5:1 to 5:1.

With regard to the preferences mentioned above in connection with thermoplastic polymer materials, polyphosphates, further constituents, and proportions, the same applies mutatis mutandis to the constituents present in the films.

In particular, the thermoplastically processable organic polymer materials present in the films consist to an extent of at least 50% by weight, based on the total mass of film material, of one or more organic thermoplastic polymers. In particular, the proportion of organic thermoplastic polymers in thermoplastic polymer materials of this kind is at least 60% by weight and especially at least 65% by weight, based on the total mass of film material. The proportion of organic polymers in thermoplastic polymer materials of this kind is frequently 50% to 99% by weight, in particular at least 60% to 97% by weight, and especially 65% to 95% by weight, based on the total mass of film material. In this group of embodiments, the polyphosphate content in the film materials is typically within a range from 1% to 30% by weight, in particular within a range from 2% to 20% by weight, and especially within a range from 3% to 15% by weight, based on the total mass of polymer material+polyphosphate.

In a preferred group of embodiments, the thermoplastically processable organic polymer materials present in the films comprise as the principal constituent, i.e. to an extent of at least 50% by weight, preferably to an extent of at least 60% by weight, in particular to an extent of at least 80% by weight or to an extent of at least 90% by weight, based on the organic polymers contained therein, a mixture comprising:
  1% to 40% by weight, in particular 2% to 30% by weight, of at least one polylactide and
  60% to 99% by weight, in particular 70% to 98% by weight, of at least one aliphatic-aromatic polyester, in particular at least one of the aliphatic-aromatic polyesters mentioned as being particularly preferred.
where the values in % by weight are based on the total mass of polylactide and aliphatic-aromatic polyester.

In a further preferred group of embodiments, the thermoplastically processable organic polymer materials present in the films comprise as the principal constituent, i.e. to an extent of at least 50% by weight, preferably to an extent of at least 60% by weight, in particular to an extent of at least 80% by weight or to an extent of at least 90% by weight, based on the organic polymers contained therein, at least one copolyester of a hydroxybutyric acid with a hydroxyalkanoic acid having 6 to 12 carbon atoms, for example at least one copolyester of a hydroxybutyric acid with a hydroxyvaleric acid, e.g. (P(3HB)-co-P(3HV)), and/or a copolyester of a hydroxybutyric acid with a hydroxyhexanoic acid, or a mixture of one or more such copolyesters with at least one polylactide.

These films optionally comprise at least one further inorganic filler. In particular, the further filler is chalk, talc, and/or mixtures thereof. The proportion of further fillers, if present, is typically within a range from 1% to 25% by weight based on the total mass of the film material. The total mass of polyphosphate and optionally present fillers different therefrom is preferably not more than 50% by weight, in particular 40% by weight, and especially 35% by weight and is typically within a range from 1% to 50% by weight, in particular within a range from 2% to 40% by weight, and especially within a range from 3% to 35% by weight, based on the film material.

Another particularly preferred group of embodiments of the invention relates to pads made from the hydrogels described above that comprise at least one crystalline inorganic polyphosphate.

Preferred pads have a thickness within a range from 4 to 20 mm and in particular within a range from 10 to 17 mm. In particular, they comprise as the crystalline inorganic polyphosphate a polyphosphate having a mass-median particle diameter $d_{50}$ within a range from 5 to 40 µm, in particular within a range from 10 to 30 µm.

With regard to the preferences mentioned above in connection with hydrogel formers, polyphosphates, further constituents, and proportions, the same applies mutatis mutandis to the constituents present in the pads.

In particular, the pads comprise as the hydrogel former at least one crosslinked polysaccharide, in particular at least one crosslinked carboxylated polysaccharide, and especially a cross-linked alginate. The crosslinking of the carboxylated polysaccharide is effected in particular by coordinative crosslinkers. In particular, crosslinking is effected by salts of polyvalent metal ions. These include in particular the abovementioned salts of the alkaline earth metals and also the abovementioned zinc salts.

In particular, the pad comprises the hydrogel former in an amount within a range from 2% to 15% by weight based on the total mass of the pad. In addition to the hydrogel former, the pad comprises water and the crystalline inorganic polyphosphate. The water content in the pad is preferably within a range from 30% to 90% by weight based on the total mass of the pad. In particular, the polyphosphate content in the pad is typically within a range from 1% to 30% by weight, in particular within a range from 2% to 20% by weight, and especially within a range from 3% to 15% by weight, based on the total mass of the pad.

The production of the agents of the invention can be effected in a manner known per se by analogy with the production of known sheet materials from polymer materials. Production typically comprises the incorporation of the polyphosphate and optionally further hemostatic agents into the organic polymer material. Processes for this are familiar to those skilled in the art.

Agents of the invention based on thermoplastic polymer materials, for example films, can be produced in a simple manner by processing the desired thermoplastic polymer with the inorganic polyphosphate and optionally with processing aids and/or other fillers into a compound and using this compound to produce a sheet material such as a film in a manner known per se, e.g. by extrusion.

Agents of the invention based on hydrogels, such as pads, can be produced in a simple manner by suspending the desired inorganic polyphosphate and optionally one or more further fillers in a solution of the uncrosslinked hydrogel former in water, effecting crosslinking of the hydrogel former, and forming a sheet material during the crosslinking process, for example by mold casting or by extrusion.

For treatment of a bleeding wound, the agent of the invention is usually applied in the wound area such that the wound or wound area is at least partially, preferably completely or largely, covered by the agent. After it has been applied, the sheet-like agent is in the immediate vicinity of the wound tissue or is in contact therewith and comes into contact with blood. Because of its flexibility, the agent is able to adapt to the shape of the wound to a certain degree and to cover the wound surfaces at least partially, or it already has the approximate shape of the wound before application. For different wounds or sources of bleeding, those skilled in the art will therefore have no difficulty in selecting the hemostatic treatment agent of the invention that is optimal in the individual case and adapting its shape to the wound area, for example by cutting it to the required size. Because of their sheet-like structure, the agents of the invention can be easily applied to the bleeding wound.

Because of their hemostatic effect, the agents of the invention are particularly suitable for treating bleeding wounds. These can be superficial skin injuries, but also injuries to body tissues, in particular damage to the tissue of internal organs, such as occurs during surgical interventions and which often result in diffuse, sometimes also profuse blood flow. The risk of the agent being washed out of the wound area or penetrating the bloodstream is ruled out by its sheet-like nature. Moreover, the applied agent can be introduced into the blood flow directly by applying pressure to the bleeding wound, with the result that the clotting occurs more efficiently.

The agents of the invention are accordingly particularly suitable for use in surgical interventions, particularly in operations on internal organs.

The agent can additionally be used in all areas of emergency medicine.

The agents of the invention are elucidated in more detail by the figures and examples that follow.

Starting Materials:
PBAT: Polybutylene adipate terephthalate, Ecoflex® from BASF SE, Ludwigshafen;
PBST: Polybutylene succinate terephthalate from IRe Chemicals Ltd., South Korea;
PLA: Polylactic acid PLA 2003D, from Nature Works;
Chalk: Commercially available chalk powder having a $d_{50}$ value of 1 μm, product from Omya GmbH, Cologne;
Talc: Commercially available talc having a $d_{50}$ value of 2.2 to 15 μm;
Maddrell salt: High-molecular-weight crystalline sodium polyphosphate in the form of a powder having a $d_{50}$ value of 15 μm, a proportion of soluble constituents of <3% by weight, a degree of crystallinity of >95%, an average number of P atoms per polyphosphate anion of 44, and a phosphate content of 70% by weight, calculated as $P_2O_5$;
Sodium alginate: Hewigum Na 1 from Hewico Produktions u. Handels GmbH having a loss on drying of <15% by weight and a particle size of 177 μm, the 1% by weight solution of which in water at 22° C. having a viscosity of 700 mPas;
$CaSO_4$: Calcium sulfate dihydrate powder, analytical grade, having a $d_{50}$ value of 10 μm (Luxopharm® F211 from SRL Pharma, Ludwigshafen);
TSPP: Tetrasodium pyrophosphate E450 (iii), BK Giulini, Ladenburg.

General Production Procedure for Films
Please specify production procedure for extrusion, with process parameters, e.g.:
A compound was produced from the starting materials listed in Table 1 in a TSA model EMP 26-40 extruder having a D/L ratio of 26:40 operated at a screw speed of 200 rpm, a nozzle upstream pressure of 14 to 15 bar, and the temperature profile shown in Table 1a.

The respective compound was processed into a film having an average thickness of 15 μm in a Leistritz model ZSE 40 film extruder having a D/L ratio of 26:40 operated at a screw speed of 180 rpm and a nozzle upstream pressure of 11 to 12 bar.

TABLE 1

| Starting material | Film 1 | Film 2 | Film 3 | Film 4 | Film 5 | Film 5 |
|---|---|---|---|---|---|---|
| PBAT [% by weight] | 63.0 | 63.0 | 63.0 | 63.0 | 63.0 | 0 |
| PBST [% by weight] | 0 | 0 | 0 | 0 | 0 | 63.0 |
| PLA [% by weight] | 10.0 | 10.0 | 10.0 | 11.0 | 15.0 | 10.0 |
| Processing aid 1 [% by weight] | 1.0 | 1.0 | 1.0 | 1.0 | 1.0 | 1.0 |
| Processing aid 2 [% by weight] | 0.5 | 0.5 | 0.5 | 0.5 | 0.5 | 0.5 |
| Chalk [% by weight] | 12.5 | 15.5 | 10.5 | 12.5 | 10.5 | 12.5 |
| Talc [% by weight] | 8.0 | 0 | 0 | 4.0 | 0 | 8.0 |
| Maddrell salt [% by weight] | 5.0 | 10.0 | 15.0 | 8.0 | 10.0 | 5.0 |

TABLE 1a

| Zone | 1 | 2 | 3 | 4 | 5 | 6 | 7 | 8 nozzle |
|---|---|---|---|---|---|---|---|---|
| Nominal | 140 | 150 | 155 | 160 | 170 | 175 | 170 | 160 |
| Actual | 140 | 150 | 160 | 170 | 170 | 175 | 171 | 162 |

General Production Procedure for Pads Made from Hydrogels

Sodium alginate and tetrasodium pyrophosphate were dissolved in water in a beaker in the amounts shown in Table 2. To this were successively added with stirring, in the amounts shown in Table 2, solid Maddrell salt and calcium sulfate dihydrate powder, tetrasodium pyrophosphate and the mixture was then stirred for a further 40 sec or 90 sec at the stirring speed shown in Table 2. Approx. 75 ml portions of the suspension thus obtained were poured into Petri dishes having a diameter of 8.5 cm and the dishes were left for 1 h at 23° C. This afforded pads having a thickness of 15 mm, a Maddrell salt content of 9% by weight, and a water content of about 85% by weight.

TABLE 2

|  | Experiment 1 | Experiment 2 | Experiment 3 |
|---|---|---|---|
| Starting material |  |  |  |
| Alginate [g] | 7.2 | 7.2 | 6.8 |
| $CaSO_4$ [g] | 5.2 | 5.2 | 4.9 |
| TSPP [g] | 1.0 | 1.5 | 1.6 |
| Maddrell salt [g] | 20 | 20 | 20 |
| Deionized water [g] | 188 | 188 | 188 |
| Reaction parameters |  |  |  |
| Stirring speed [rpm] | 1000 | 1000 | 1000 |
| Stirring time [sec] | 90 | 40 | 40 |
| Product characteristics | flexible | flexible | flexible |
| Water content [% by weight] | 84.9% | 84.72% | 84.95% |
| Content of Maddrell salt [% by weight] | 9% | 9% | 9% |

The following investigations were carried out to determine the hemostatic effect of the sheet materials of the invention by comparison with a commercially available wound dressing.

The wound dressings employed were the inventive film 3 shown in Table 1, hereinafter referred to as TS, and the commercial kaolin-containing textile wound dressing QuickClot Combat Gauze® (Z-Medica), hereinafter RS.

26 domestic pigs (79±2.4 kg) were divided into two groups, which were treated either with film TS (n=14) or with wound dressing RS (n=12). After measurement of baseline systemic hemodynamics and local transit time flow measurement (TTFM) on the femoral artery, a standardized complex groin injury was executed by means of a 4.7 mm puncture of the femoral artery proximal to the flow probe. Uncontrolled bleeding was facilitated in order to achieve a target arterial systolic pressure of less than 60 mmHg as an indicator of severe shock. All wound dressings were applied for 5 minutes, with application of 200 mmHg continuous pressure. After 5 minutes the pressure was released and hemostasis was restored. The hemodynamic baseline values were restored by volume replacement and catecholamines and hematological parameters were recorded for two hours. Response-variable data were presented in the form of a failure time distribution, the time to event being defined as the time to cessation of hemostasis or until the end of the experiment. The data were analyzed by the Kaplan-Meier method and with the aid of several Cox regressions. Independent variables included directly measured hemodynamic variables and the difference between the values for the event time, which were calculated as the difference from baseline and from shock induction.

In all 26 of the 26 animals, the wound dressing achieved hemostasis during revival after the shock event. Renewed bleeding occurred in 10 out of the 26 treated pigs. 3/12 (25%) of the animals treated with RS and 7/14 (50%) of the animals treated with TS had renewed bleeding (p=0.19). The time to renewed bleeding showed no significant difference between the groups (median: TS 45 min vs. RS 50 min, p<0.983). There was no statistically significant difference in femoral arterial blood flow between the two groups and the result was comparable.

The invention claimed is:

1. An agent for use in treating bleeding wounds in mammals, in the form of a flexible sheet material formed from an organic polymer material comprising at least one particulate crystalline inorganic polyphosphate, wherein the organic polymer material forms a sheet-like continuous matrix in which the particles of the particulate crystalline inorganic polyphosphate are present in the organic polymer material in finely divided form, such that the polymer material at least partly surrounds the particles of the particulate crystalline inorganic polyphosphate distributed therein, the polyphosphate at 20° C. having a solubility in deionized water of less than 5 g/L and the anion of the polyphosphate having a number average of at least four phosphorus atoms per polyphosphate anion.

2. The agent as claimed in claim 1, wherein the polyphosphate is selected from alkali metal polyphosphates, alkaline earth metal polyphosphates, and ammonium polyphosphates.

3. The agent as claimed in claim 1, wherein the polyphosphate is a sodium polyphosphate.

4. The agent as claimed in claim 1, wherein the particles of the polyphosphate have a mass-median particle diameter, determined by static laser-light scattering, within a range from 5 to 40 μm.

5. The agent as claimed in claim 1, comprising the polyphosphate in an amount within a range from 1% to 30% by weight based on the total weight of the agent.

6. The agent as claimed in claim 1, wherein the organic polymer material is thermoplastic.

7. The agent as claimed in claim 6, wherein the organic polymer material comprises as the principal constituent, based on the organic polymers contained therein, at least one polymer selected from polyhydroxyalkanoates, polylactides, aliphatic-aromatic polyesters, aliphatic-aromatic polyamides, polyolefins, polysiloxanes, and mixtures thereof.

8. The agent as claimed in claim 7, wherein the organic polymer material comprises as the principal constituent, based on the organic polymers contained therein,
   i. a mixture of at least one polylactide and at least one aliphatic-aromatic polyester; or
   ii. at least one copolyester of a hydroxybutyric acid with a hydroxyalkanoic acid having 6 to 12 carbon atoms, or a mixture of such a copolyester with polylactide.

9. The agent as claimed in claim 6 in the form of a film.

10. The agent as claimed in claim 9, wherein the ratio of film thickness to median particle diameter of the particulate polyphosphate is within a range from 0.5:1 to 5:1.

11. The agent as claimed in claim 1, wherein the organic polymer material is in the form of a hydrogel based on an organic polymer.

12. The agent as claimed in claim 11, wherein the organic polymer material comprises as the principal constituent, based on the organic polymers contained therein, at least one hydrogel-forming polysaccharide.

13. The agent as claimed in claim 11, wherein the organic hydrogel-forming polysaccharide is a cross-linked alginate.

14. The agent as claimed in claim 11 in the form of a pad.

15. The agent as claimed in claim 1, which is packaged sterile.

16. A method for treating a mammal having a bleeding wound, comprising applying the agent of claim 1 to a wound area.

17. The method of claim 16, wherein the mammal had previously been treated with an agent that reduces blood clotting or has a coagulopathy.

18. A process for producing the agent as claimed in claim 1, comprising the incorporation of the crystalline inorganic polyphosphate and optionally further hemostatic agents into the organic polymer material, such that the polymer material at least partly surrounds the particles of the particulate crystalline inorganic polyphosphate distributed therein.

19. The method of claim 16, wherein the treating occurs during a surgical intervention.

20. The method of claim 19, wherein the surgical intervention is an operation on an internal organ.

* * * * *